(12) United States Patent
Violand et al.

(10) Patent No.: US 6,653,098 B1
(45) Date of Patent: Nov. 25, 2003

(54) METHOD OF PRODUCING MOUSE AND HUMAN ENDOSTATIN

(75) Inventors: Bernard N. Violand, Glencoe, MO (US); Elizabeth I. Harding, Kirkwood, MO (US)

(73) Assignee: G. D. Searle & Co., Skokie, IL (US)

( * ) Notice: Subject to any disclaimer, the term of this patent is extended or adjusted under 35 U.S.C. 154(b) by 0 days.

(21) Appl. No.: 09/231,077

(22) Filed: Jan. 14, 1999

Related U.S. Application Data

(60) Provisional application No. 60/075,587, filed on Feb. 23, 1998.

(51) Int. Cl.[7] .................. C12N 15/00; C07H 21/02; C07H 21/04; C07K 14/00
(52) U.S. Cl. .................. 435/69.1; 435/252.33; 435/252.5; 435/254.2; 435/348; 435/325; 435/366; 435/320.1; 536/23.1; 530/350
(58) Field of Search .................. 435/69.1, 252.33, 435/252.5, 254.2, 348, 325, 366, 320.1; 536/23.1; 530/350

(56) References Cited

U.S. PATENT DOCUMENTS 5,854,205 A * 12/1998 O'Reilly et al. ............... 514/2

FOREIGN PATENT DOCUMENTS

| EP | 0 219 874 A | 4/1987 |
|---|---|---|
| EP | 0 312 358 A | 4/1989 |
| EP | 0 393 725 A | 10/1990 |
| WO | WO 96 40736 | 12/1996 |
| WO | WO 97 15666 | 5/1997 |
| WO | WO 97 18233 A | 5/1997 |

OTHER PUBLICATIONS

Cohen, J. Behind the headlines of endostatin's ups and downs. Science 283:1250–1251, Feb. 1999.*
Dhanabal et al. Endostatin: Yeast production, mutants and antitumor effect in renal cell carcinoma. Cancer Research 59:189–197, Jan. 1999.*
Kohno et al. Refolding of recombinant proteins. Methods in Enzymology 185:187–195, 1990.*
Cohen et al. Endostatin: An endogenous inhibitor of angiogenesis and tumor growth. Cell vol. 88, pp. 277–285, Jan. 1997.*
O'Reilly M. S. et al.: "Endostatin: an endogenous inhibitor of angiogenesis and tumor growth" Cell, vol. 88, No. 88, (Jan. 24, 1997), pp. 277–285.
Dhanabal et al.: "Endostatin: Yeast production mutants, and antitumor effect in renal cell carcinoma" Cancer Research, vol. 59, No. 1 (Jan. 1, 1999), pp. 189–197.
Standker L. et al.: "Isolation and characterization of the circulating form of human endostatin" Febs Lett., vol. 420, (1997), p. 129–133.
Hermann R. "Standard techniques for protein solubilisation and unfolding" Protein Folding, (1993), pp. 1–6, 13–16, 50–53, 89–92, 107–111.

* cited by examiner

Primary Examiner—Christopher S. F. Low
Assistant Examiner—Chih-Min Kam
(74) Attorney, Agent, or Firm—Verne A. Luckow

(57) ABSTRACT

Methods for producing mouse and human endostatin are disclosed. Methods for refolding and purifying endostatin from inclusion bodies expressed in bacteria and nucleic acids encoding full-length and truncated forms of endostatin are also disclosed.

26 Claims, 10 Drawing Sheets

SOLUBILIZATION OF IBS IN

6 M UREA, 5 mM DTT (mouse) or 10 mM cysteine (human), pH 10.8

MIX 2 HOURS

ADDITION OF 10 mM CYSTINE,

MIX 5 MINUTES

DILUTE 10-FOLD TO 3.5 M Urea (Mouse) or 3.0 M Urea (Human) and pH 7.0 (Mouse) or pH 7.5 (Human)

STIR 60 HOURS

METHOD OF PRODUCING MOUSE AND HUMAN ENDOSTATIN

PRIORITY

The present application claims priority under Title 35, United States Code, §119 of U.S. Provisional Application Serial No. 60/075,587 filed Feb. 23, 1998.

FIELD OF THE INVENTION

Methods for producing mouse and human endostatin are disclosed. Methods for refolding and purifying endostatin from inclusion bodies expressed in bacteria and nucleic acids encoding full-length and truncated forms of endostatin are also disclosed.

BACKGROUND OF THE INVENTION

Angiogenesis

Angiogenesis, the growth of new blood vessels, plays an important role in cancer growth and metastasis. In humans, the extent of vasculature in a tumor has been shown to correlate with the patient prognosis for a variety of cancers (Folkman, J., *Seminars in Medicine of the Beth Israel Hospital*, Boston 333(26): 1757–1763, 1995; Gasparini, G., *European Journal of Cancer* 32A(14): 2485–2493, 1996; Pluda, J. M., *Seminars in Oncology* 24(2): 203–218, 1997; Norrby, K, APMIS 105: 417–437, 1997). In normal adults, angiogenesis is limited to well controlled situations, such as wound healing and the female reproductive system (Battegay, E. J., *J Mol Med* 73:-333–346, 1995; Dvorak, H. F, *New Engl J Med*, 315: 1650–1659, 1986).

Animal studies suggest that tumors can exist in a dormant state, in which tumor growth is limited by a balance between high rates of proliferation and high rates of apoptosis (Holmgren, L. et al., *Nat. Med.* (N. Y.) 1(2): 149–153, 1995; Hanahan, D. et al., *Cell* 86(3): 353–364, 1996). The switch to an angiogenic phenotype allows tumor cells to escape from dormancy and to grow rapidly, presumably as the result of a decrease in the apoptotic rate of the tumor cells (Bouck, *Cancer Cells*, 2(6): 179–185, 1990; Dameron et al, *Cold Spring Harb Symp Quant Biol*, 59: 483–489, 1994). The control of angiogenesis is thought to be a balance between factors which promote new vessel formation and anti-angiogenic factors with suppress the formation of a neovasculature (Bouck, N. et al., *Advances in Cancer Research* 69: 135–173, 1996; O'Reilly et al., Cell 79(2): 315–328, 1994).

A variety of pro-angiogenic factors have been characterized including basic and acid fibroblast growth factors (bFGF and aFGF) and vascular permeability factor/vascular endothelial growth factor (VPF/VEGF) (Potgens, A. J. G. et al., *Biol. Chem. Hoppe-Seyler* 376: 57–70, 1995; Ferrara, N., *European Journal of Cancer* 32A(14): 2413–2442, 1996; Bikfalvi, A. et al., *Endocrine Reviews* 18: 26–45, 1997). Several endogenous anti-angiogenic factors have also been characterized, including angiostatin (O'Reilly et al., *Cell* 79(2): 315–328, 1994), endostatin (O'Reilly et al, *Cell* 88(2): 277–285, 1997), interferon-alpha. (Ezekowitz et al, *N. Engl. J. Med.*, May 28, 326(22) 1456–1463, 1992), thrombospondin (Good et al, *Proc Natl Acad Sci* USA 87(17): 6624–6628, 1990; Tolsma et al., J Cell Biol 122(2): 497–511, 1993), and platelet factor 4 (PF4) (Maione et al, *Science* 247(4938): 77–79, 1990).

Many angiogenic inhibitors are in clinical development (See Shawver et al., *Drug Discovery Today* 2(2): 50–63, 1997, and references therein). Polypeptides such as interferon alpha and platelet factor 4 are in clinical trials. Angiostatin, soluble Flt-1 receptor, and bactericidal/permeability increasing protein derivative 23 are in preclinical studies. Monoclonal antibodies such as humanized anti-$a_vb_3$ antibody (LM609), anti-VEGF, and anti-Flk-1 monoclonal antibody (DC101) are also in preclinical studies. Tecogalan (DS4152), a sulfated polysaccharide-peptidoglycan complex is in clinical trials, and bFGF carbohydrate inhibitor (GM1474) and glyceptor mimetic inhibitor of bFGF (GL14.2) are in preclinical studies. The antibiotic AGM1470 (TNP470), a fumagillin analog, and Suramin, a polyanionic compound are in clinical trials. Small molecule inhibitors such as urokinase receptor antagonists, inhibitors of phospatidic acid, inhibitors of Flk-1, and inhibitors of VEGF-F11 binding are all in preclinical studies. Thalidomide, and its analogues, and matrix metalloproteinase inhibitors, such as Batimastat/Marimastat, are in clinical trials. Oligonucleotides, such as ribozymes that target VEGF receptors and VEGF anti-sense oligonucleotides, are also in preclinical trials.

Anti-angiogenic therapy may offer several advantages over conventional chemotherapy for the treatment of cancer. Anti-angiogenic agents have low toxicity in preclinical trials and development of drug resistance has not been observed (Folkman, J., *Seminars in Medicine of the Beth Israel Hospital*, Boston 333(26): 1757–1763, 1995). As angiogenesis is a complex process, made up of many steps including invasion, proliferation and migration of endothelial cells, it can be anticipated that combination therapies may be most effective. In fact, combinations of chemotherapy with anti-angiogenic therapy have already shown promising results in pre-clinical models (Teicher, B. A. et al., *Breast Cancer Research and Treatment* 36: 227–236, 1995; Teicher, B. A. et al., *European Journal of Cancer* 32A(14): 2461–2466, 1996).

Endostatin

Endostatin is a 20 kDa protein derived from the C-terminal fragment of alpha 1 type collagen XVIII. Conditioned cell culture media from a hemangioendothelioma cell line (EOMA) was shown to contain a factor which inhibited endothelial cell proliferation in vitro (O'Reilly et al., *Cell* 88: 277–285, 1997). The factor responsible for this inhibition was named endostatin. A recombinant form of this protein expressed in baculovirus-infected insect cells inhibited the growth of metastases in the Lewis lung tumor model and an insoluble *E. coli* derived form of this protein was shown to be efficacious in preventing primary tumor growth in several tumor models (O'Reilly et al., *Cell* 88: 277–285, 1997; Boehm et al., *Nature* 390: 404–410, 1997).

Purification and Refolding of Endostatin

Although many types of expression systems have been developed over the past twenty years, bacterial systems, particularly those based on *E. coli*, are widely used for the production of proteins on an industrial scale. Vectors which permit high level expression and the ability to carry out fermentations at high cell densities and low cost, have contributed to the extensive development and use of *E. coli*-based expression systems. One significant problem, however, is the tendency of *E. coli* to form inclusion bodies which contain the desired recombinant protein. Inclusion body formation necessitates additional downstream processing, such as in vitro refolding, before biologically active proteins can be recovered. The tendency to form insoluble aggregates does not appear to correlate with factors such as size, hydrophobicity, subunit structure, or the use of fusion domains (Kane J. F. and Harley, D. L., *Tibtech* 6: 95, 1988). Inclusion body formation appears to be determined by the rates of protein synthesis, folding, aggregation, and proteolytic degradation, the solubility and thermodynamics of folding intermediates and native proteins, and the interactions of these species with chaperone proteins (Rainer Rudolph, In Protein Engineering: Principles and Practice, Edited by Jeffrey L. Cleland and Charles S. Craik, p 283–298, Wiley-Liss, Inc., New York, N.Y., 1996).

Inclusion bodies generally form in the cytoplasm of cells expressing a recombinant protein at high levels. They refract light when observed by phase contrast microscopy and thus are sometimes referred to as refractile bodies. The inclusion bodies are characterized by a relatively high specific density and can be pelleted from lysed cells by centrifugation. The formation of inclusion bodies may protect recombinant proteins from proteolysis as they do not easily disintegrate under physiological solvent conditions. High concentrations of denaturants, such as 6 M guanidine hydrochloride or 6–8 M urea, have been commonly used to solubilize the proteins present in inclusion bodies. A variety of inclusion body solubilization protocols have been compared (Fisher, B., Summer, L. and Goodenough, P. *Biotechnol. Bioeng.* 1: 3–13, 1992).

Although the desired foreign gene product is the main component of inclusion bodies, other host cell proteins such as small heat shock proteins, outer membrane proteins, elongation factor EF-TU, and RNA polymerase may also be enriched in such preparations (Allen, S. P., Polazzi, J. O. Gierse, J. K., and Easton, A. M., *J. Bacteriol.* 174: 6938–6947, 1992); Hart, R. A., Rinas, U., and Bailey, J. E., *J. Biol. Chem.* 265: 12728–12733, 1990; Hartley, D. L., and Kane, J. F., *Biochem. Soc. Trans.* 16: 101, 1988).

World patent application WO 97/15666 describes the expression, purification, and characterization of endostatin from *E. coli* and baculovirus-infected insect cells. The bacterially-derived endostatin was not refolded into its native state, but was utilized as an insoluble suspension for most of these studies. This disclosure also describes the purification of native endostatin from conditioned media of the murine hemangioendothelioma cell line EOMA. Endostatin was purified from this conditioned media through classical purification methodology.

No successful attempts at refolding endostatin have been described (O'Reilly et al., *Cell* 88: 277–285, 1997). The *E. coli*-derived recombinant endostatin characterized by these authors precipitated following dialysis against PBS. The precipitated (nonrefolded) material could not be tested in vitro because of its insolubility in culture media. A small (unspecified) percentage of the material spontaneously solubilized in the PBS during dialysis. This material had comparable inhibitory activity in endothelial cell activities as both native and soluble baculovirus-derived endostatin. When the *E. coli*-derived recombinant endostatin was refolded in the presence of 0.1 M sodium phosphate, pH 7.4, 150 mM NaCl, 0.6 M urea, 2 mM reduced glutathione, 0.02 mM oxidized glutathione, and 0.5 M arginine at a final concentration of 0.1 mg/ml, over 99% of the protein was lost. This great loss precluded use of this material for in vivo assays. Instead, the authors used the uncharacterized insoluble (nonrefolded) form of endostatin for most of their in vivo studies. The *E. coli*-derived endostatin precipitate was observed to dissolve gradually over five days and produce a sustained anti-angiogenic effect in chick chorioallantoic membrane (CAM) assays. A suspension of the same material formed a pellet at the site of injection in mice, which resorbed slowly over a 24–48 hour period.

Subsequent studies by the same group demonstrated that drug resistance does not develop when mice bearing lung carcinoma, T241 fibrosarcoma, or B16F10 melanoma are treated with mouse endostatin (Boehm, T., et al., *Nature* 390: 404–407, 1997). *E. coli*-derived recombinant murine endostatin was prepared as described earlier (O'Reilly et al., *Cell* 88: 277–285, 1997) except that bacteria were pelleted and resuspended in 8 M urea, 10 mM beta mercaptoethanol, and 10 mM pH 8.0, and incubated for 1 to 2 hours. Beta mercaptoethanol was eliminated in subsequent steps. Recombinant mouse endostatin was delivered to mice as a suspension in PBS. Mice bearing one of the three tumor types were injected with the purified but poorly soluble endostatin suspension into the subcutaneous dorsa at a site remote from the inoculated tumors. Treatment was stopped when tumors regressed, then allowed to regrow. Tumor growth did not recur after 6, 4, or 2 endostatin treatment cycles, respectfully, when therapy was ended.

Recently, the circulating form of human endostatin was isolated and characterized (Standker et al., FEBS *Letters* 420: 129–133, 1997). High molecular weight peptides (1–20 kDa) were isolated from 2,500 liters of human blood ultrafiltrate (hemofiltrate, HF) obtained from patients with chronic renal insufficiency. Extracts were bound to a preparative cation exchange column and eluted by pH pool fractionation (7 buffers with pH increasing from 3.6 to 9.0). High molecular weigh peptides were detected in pool 8, which was eluted with water, and subsequently purified by reversed-phase HPLC. Aliquots were subjected to matrix-assisted laser desorption ionization mass spectrometry (MALDI-MS) and the exact molecular mass determined by electrospray mass spectroscopy (ES-MS) was found to be 18,494 Da. Cysteine residues 1–3 and 2–4 in the molecule were found to be linked by disulfide bridges. The final recovery during purification was estimated to be in the range of 20%, resulting in a concentration of $>10^{-11}$ M in hemofiltrate. The resulting concentration of endostatin in patient plasma was estimated to be in the range of $10^{-10}$ M or higher. It is not known if pool of tissue bound endostatin exists, as was proposed for angiostatin (Kost et al., *Eur J. Biochem.* 236: 682–688, 1996). In vitro biological characterization of the native human endostatin (which was 12 amino acids shorter than mouse endostatin) showed no anti-proliferative activity on different endothelial cell types. The characterization of recombinant forms of human endostatin was not reported. The authors speculate that differences in reported activity of mouse and human forms of endostatin could be due to several factors: (i) the two forms may were isolated from different sources and may have different selectivity, specificity, or efficacy in in vitro and in vivo assays. (ii) Differences in post-translational modifications found on the peptides may account for the discrepancy in reported activities. (iii) Human endostatin may not necessarily inhibit proliferation of endothelial cells, but indirectly influence other cellular components which are observable only in a complex in vivo system.

SUMMARY OF THE INVENTION

One object of the invention is to describe a method for expressing high levels of endostatin in bacteria.

Another aspect of the invention is to describe an efficient method by which endostatin inclusion bodies can be solubilized, subsequently refolded, and purified to generate biologically-active material.

Preferably the steps of solubilizing mouse or human endostatin inclusion bodies are carried out at an elevated pH.

Preferably the elevated pH in the solubilizing step is carried out at a pH ranging from about pH 9 to about pH 11.5. Even more preferably the elevated pH range is from about pH 10 to about pH 11. Most preferably, the elevated pH is about 10.5.

Preferably the steps of refolding mouse or human endostatin inclusion bodies are carried out at a near-neutral pH. Preferably the near-neutral pH in the solubilizing step is carried out at a pH ranging from about pH 6 to about pH 8.5. Even more preferably the near-neutral pH range for refolding mouse endostatin is from about pH 7.0 to about pH 8.0. Most preferably, near-neutral pH range for refolding mouse endostatin is about pH 7.5. Even more preferably the near-neutral pH range for refolding human endostatin is from about pH 7.0 to about pH 8.0. Most preferably, near-neutral pH range for refolding human endostatin is about pH 7.5.

Preferably, the concentration of endostatin gene product is present at a concentration of from about 0.2 to about 20 mg/ml during the solubilization step. Even more preferably, the concentration is about 2.5 mg/ml.

Preferably, the concentration of endostatin gene product is present at a concentration of from about 0.02 to about 2 mg/ml during the refolding step. Even more preferably, the concentration is about 0.25 mg/ml.

Preferably a denaturant selected from urea and guanidine hydrochloride is used during the solubilization and refolding steps. Even more preferably, the denaturant is urea.

Preferably the concentration of urea is from about 4 M to about 10 M during the solubilization step. Even more preferably, the concentration is about 6 M.

Preferably the concentration of urea is from about 2 M to about 4 M during the refolding step. Even more preferably, the concentration is about 3.5 M.

Preferably the concentration of guanidine hydrochloride is from about 2 M to about 8 M during the solubilization step. Even more preferably, the concentration is about 4 M.

Preferably the concentration of guanidine hydrochloride is from about 0.2 M to about 2 M during the refolding step. Even more preferably, the concentration is about 1.5 M.

Preferably, the solubilization and reducing steps are carried out in the presence of a reducing agent capable of reducing disulfide linkages to sulfhydryl groups. Preferably the reducing agent is selected from the group consisting of DTT, BME, cysteine, and reduced glutathione. Even more preferably, the reducing agent is DTT or cysteine.

Preferably, DTT is present at a concentration of from about 2 mM to about 10 mM during the solubilization step. Even more preferably, the concentration is about 5 mM.

Preferably, DTT is present at a concentration of from about 0.5 mM to about 2 mM during the refolding step. Even more preferably, the concentration is about 0.5 mM.

Preferably, reduced glutathione is present at a concentration of from about 5 mM to about 20 mM during the solubilization step. Even more preferably, the concentration is about 10 mM.

Preferably, reduced glutathione is present at a concentration of from about 0.5 mM to about 4 mM during the refolding step. Even more preferably, the concentration is about 1 mM.

Preferably, cysteine is present at a concentration of from about 5 mM to about 20 mM during the solubilization step. Even more preferably, the concentration is about 10 mM.

Preferably, cysteine is present at a concentration of from about 0.5 mM to about 4 mM during the refolding step. Even more preferably, the concentration is about 1 mM.

Preferably, an agent capable of enhancing the interchange of disulfide bonds is present during the refolding step. Preferably the agent is selected from cystine and oxidized glutathione. Even more preferably, the agent is cystine.

Preferably, cystine is present at a concentration of from about 0.2 mM to about 5 mM during the refolding step. Even more preferably, the concentration is about 1 mM.

Preferably disulfide bonds are formed through air oxidation during the refolding step. Preferably, the air oxidation step is carried out from about 12 to about 96 hours. Even more preferably, the air oxidation step is carried out from about 24 to about 72 hours. Most preferably the air oxidation step is carried out about 60 hours.

Preferably refolded endostatin is further purified by a process selected from but not limited to the group consisting of ion-exchange chromatography, hydrophobic interaction chromatography and RP-HPLC.

Preferably the method of expression, solubilization, refolding and purification uses endostatin genes that are either mouse or human. Even more preferably these genes are selected from the group consisting of SEQ ID NOs: 5–9.

Novel proteins of this invention are modified human or mouse endostatin amino acid sequences, and said protein can optionally be immediately preceded by (methionine$^{-1}$), (alanine$^{-1}$), (methionine$^{-2}$, alanine$^{-1}$), (serine$^{-1}$), (methionine$^{-2}$, serine$^{-1}$), (cysteine$^{-1}$), or (methionine$^{-2}$, cysteine$^{-1}$).

Additionally, the present invention relates to recombinant expression vectors comprising nucleotide sequences encoding endostatin, variants and muteins of endostatin, related microbial and eukaryotic expression systems, and processes for making (comprising the steps of expressing, solubilizing, refolding, purifying) these proteins.

Cloning of DNA sequences encoding these proteins may be accomplished by the use of intermediate vectors. Alternatively, one gene can be cloned directly into a vector containing the other gene. Linkers and adapters can be used for joining the DNA sequences, as well as replacing lost sequences, where a restriction site was internal to the region of interest. Thus genetic material (DNA) encoding one polypeptide, peptide linker, and the other polypeptide is inserted into a suitable expression vector which is used to transform bacteria, yeast, insect cells or mammalian cells. The transformed organism or cell line is grown and the protein isolated by standard techniques. The resulting product is therefore a new protein which has all or a portion of one protein joined by a linker region to all or a portion of second protein.

Another aspect of the present invention includes plasmid DNA vectors for use in the expression of these proteins. These vectors contain the novel DNA sequences described above which code for the novel polypeptides of the invention. Appropriate vectors which can transform microorganisms or cell lines capable of expressing the proteins include expression vectors comprising nucleotide sequences coding for the proteins joined to transcriptional and translational regulatory sequences which are selected according to the host cells used.

Vectors incorporating modified sequences as described above are included in the present invention and are useful in the production of the proteins. The vector employed in the method also contains selected regulatory sequences in operative association with the DNA coding sequences of the invention and which are capable of directing the replication and expression thereof in selected host cells.

Methods for producing these proteins is another aspect of the present invention. The method of the present invention involves culturing suitable cells or cell lines, which has been transformed with a vector containing a DNA sequence coding for expression of a novel multi-functional protein. Suitable cells or cell lines may be bacterial cells. For example, the various strains of *E. coli* are well-known as host cells in the field of biotechnology. Examples of such strains include *E. coli* strains JM101 (Yanisch-Perron et al. *Gene* 33: 103–119, 1985) and MON105 (Obukowicz et al., *Applied Environmental Microbiology* 58: 1511–1523, 1992). Also included in the present invention is the expression of the multi-functional proteins utilizing a chromosomal expression vector for *E. coli* based on the bacteriophage Mu (Weinberg et al., *Gene* 126: 25–33, 1993). Various strains of *B. subtilis* may also be employed in this method. Many strains of yeast cells known to those skilled in the art are also available as host cells for expression of the polypeptides of the present invention.

When expressed in the *E. coli* cytoplasm, the gene encoding the proteins of the present invention may also be constructed such that at the 5' end of the gene codons are added to encode $Met^{-2}$-$Ala^{-1}$, $Met^{-2}$-$Ser^{-1}$, $Met^{-2}$-$Cys^{-1}$, or $Met^{-1}$ at the N-terminus of the protein. The N termini of proteins made in the cytoplasm of *E. coli* are affected by post-translational processing by methionine aminopeptidase (Ben Bassat et al., *J. Bacteriol.* 169:751–757, 1987) and possibly by other peptidases so that upon expression the methionine is cleaved off the N-terminus. The proteins of the present invention may include polypeptides having $Met^{-1}$, $Ala^{-1}$, $Ser^{-1}$, $Cys^{-1}$, $Met^{-2}$-$Ala^{-1}$, $Met^{-2}$-$Ser^{-1}$, or $Met^{-2}$-$Cys^{-1}$ at the N-terminus. These mutant proteins may also be expressed in *E. coli* by fusing a secretion signal peptide to the N-terminus. This signal peptide is cleaved from the polypeptide as part of the secretion process.

DEFINITIONS

The following is a list of abbreviations and the corresponding meanings as used interchangeably herein:

g=gram(s)
HPLC=high performance liquid chromatography
mg=milligram
ml=milliliter
DTT=dithiothreitol
RT=room temperature
PBS=phosphate buffered saline The following is a list of definitions of various terms used herein:

The term "anti-tumor" means possessing an activity which slows or abolishes the growth of, or which kills, or otherwise harms tumors in vivo.

The term "native sequence" refers to an amino acid or nucleic acid sequence which is identical to a wild-type or native form of a gene or protein.

The terms "mutant amino acid sequence," "mutant protein", "variant protein", "mutein", or "mutant polypeptide" refer to a polypeptide having an amino acid sequence which varies from a native sequence due to amino acid additions, deletions, substitutions, or any combination thereof, or is encoded by a nucleotide sequence from an intentionally-made variant derived from a native sequence or chemically synthesized.

The term "endostatin" means a protein fragment of collagen XVIII having anti-angiogenic activity. The activity of said fragments can be determined by the mouse corneal micropocket assay of angiogenesis or by inhibition of endothelial cell growth or migration in vitro. Preferably, mouse endostatin means the sequence depicted in SEQ ID 10, and human endostatin means the sequence depicted in SEQ ID NO 11.

The C-terminal fragment of collagen XVIII is shown. Plasmid pMON24345 (SEQ ID NO: 8) encodes the C-terminal fragment of mouse collagen XVIII, Plasmid pMON20440 (SEQ ID NO: 9) encodes the C-terminal fragment of human collagen XVIII.

Figure 1:
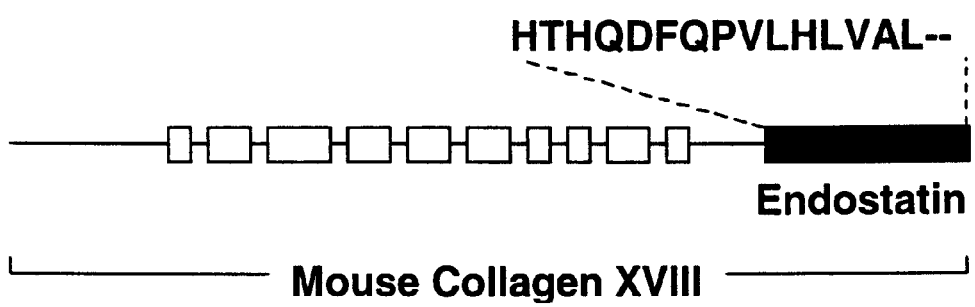
FIG. 1 shows a schematic of the cloned endostatin fragment
Figure 1:
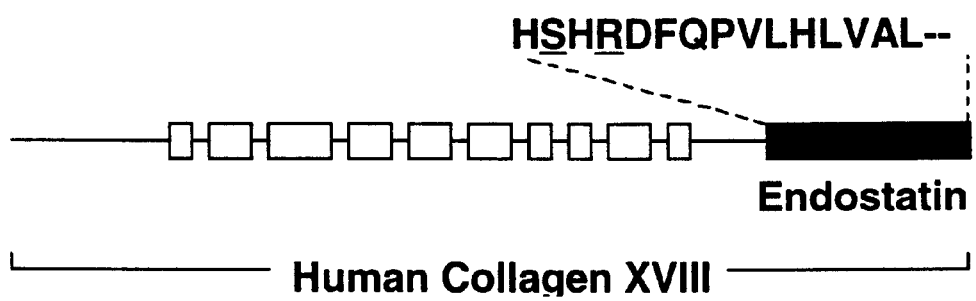
Figure 2:
Figure 2:

FIG. 2 shows a schematic of the endostatin refolding procedure

Optimal solubilization conditions in the presence of urea and DTT or cysteine and refolding in the presence of cystine are outlined.

Figure 3A:
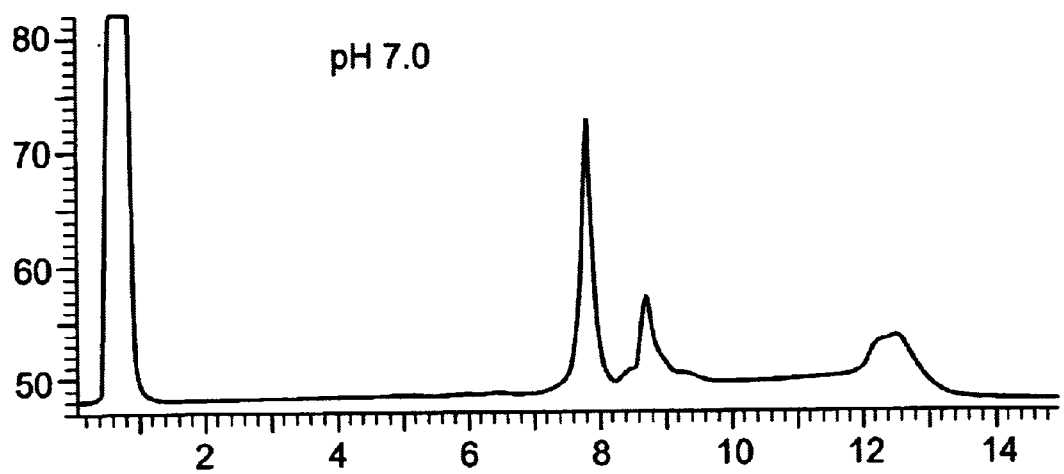
Figure 3B:
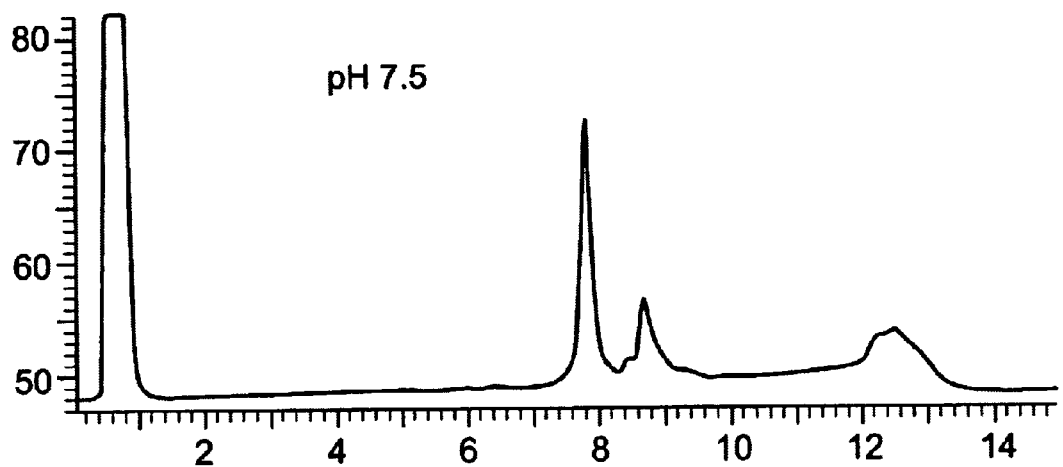
Figure 3C:
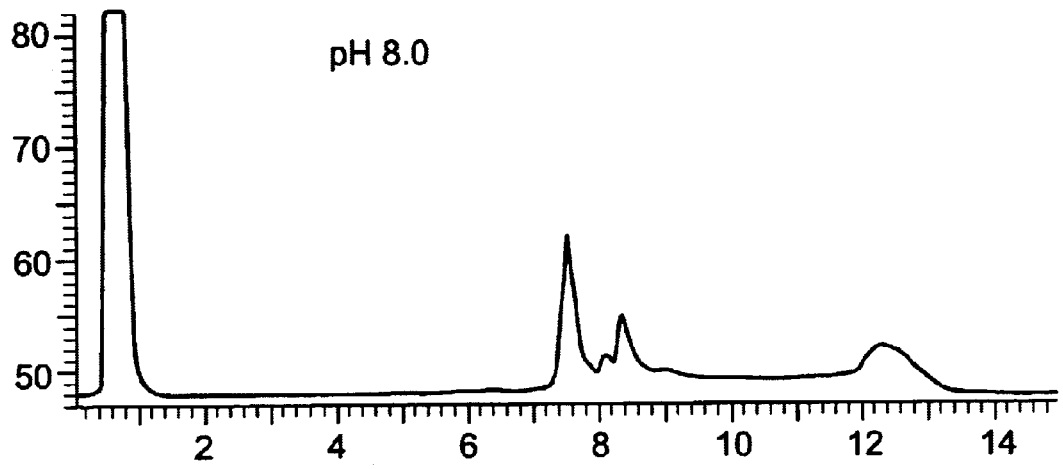

FIG. 3 shows mouse endostatin refold products under varying pH conditions

RP-HPLC tracings of mouse endostatin refold products at pH 7.5, pH 8.0, and pH 8.5 in 3.5 M urea.

Figure 4A:
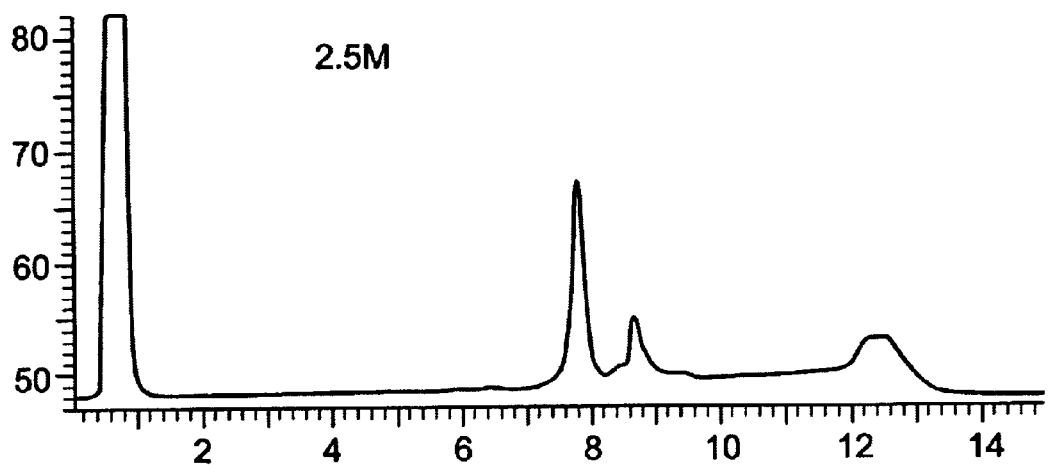
Figure 4B:
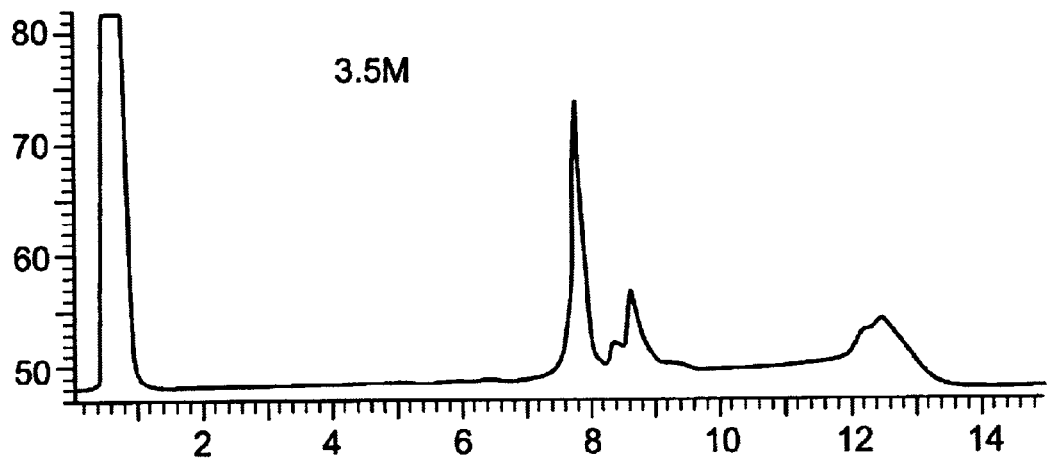
Figure 4C:
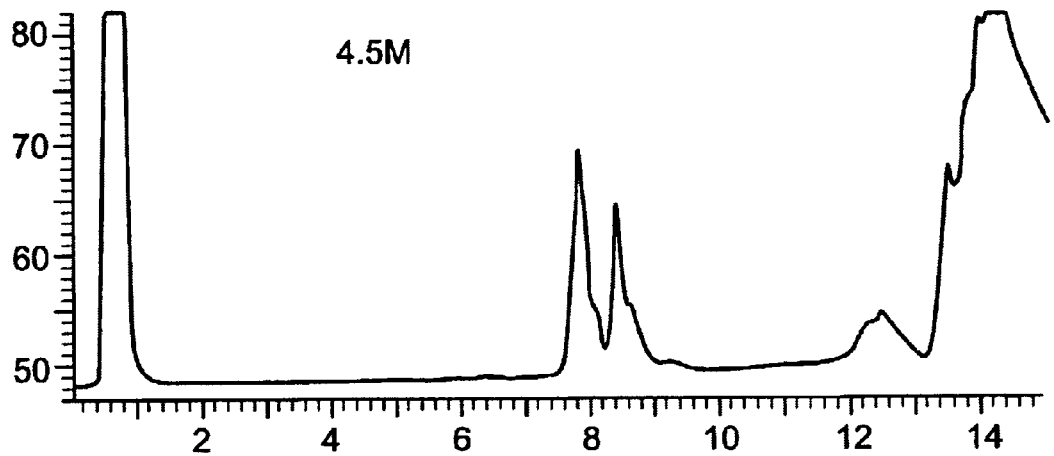

FIG. 4 shows mouse endostatin refold products under varying urea concentrations RP-HPLC tracings of mouse endostatin refold products at 3.0, 3.5, and 4.0 M urea at pH 7.5.

Figure 5A:
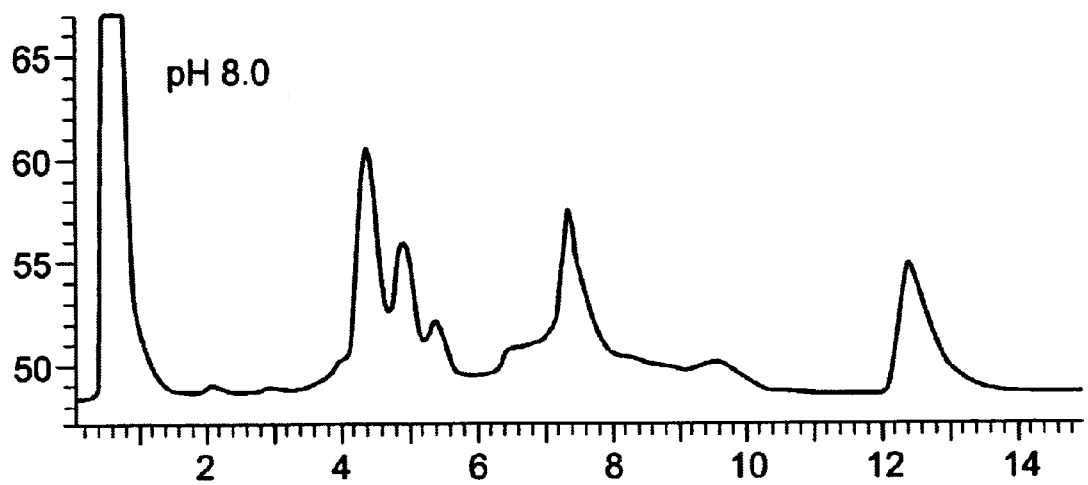
Figure 5B:
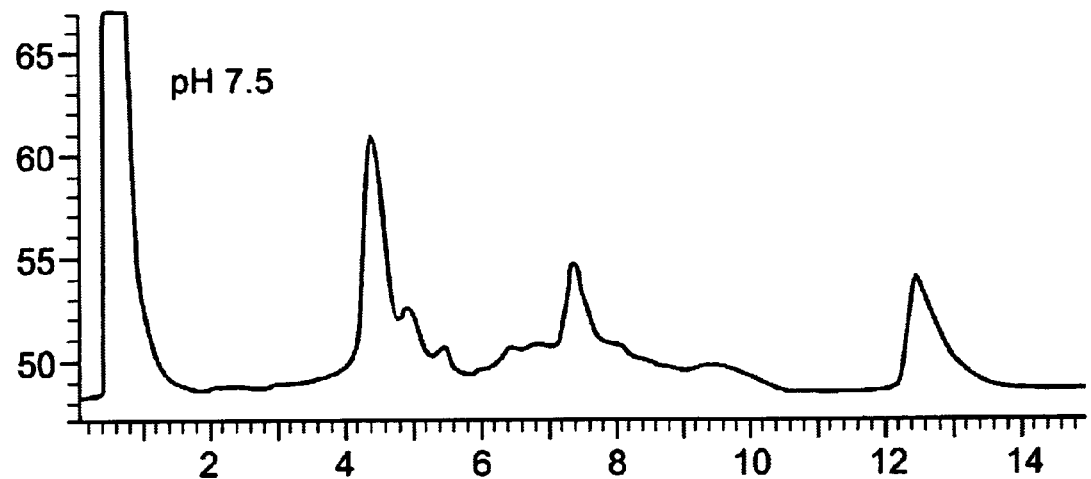
Figure 5C:
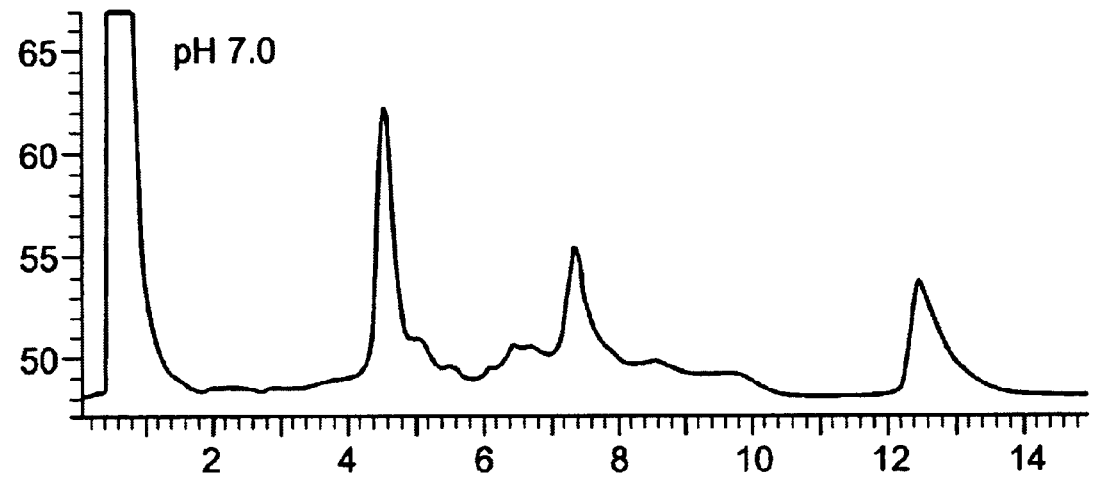

FIG. 5 shows human endostatin refold products under varying pH conditions

RP-HPLC tracings of human endostatin refold products at pH 7.5, pH 8.0, and pH 7.5 in 3.5 M urea.

Figure 6A:
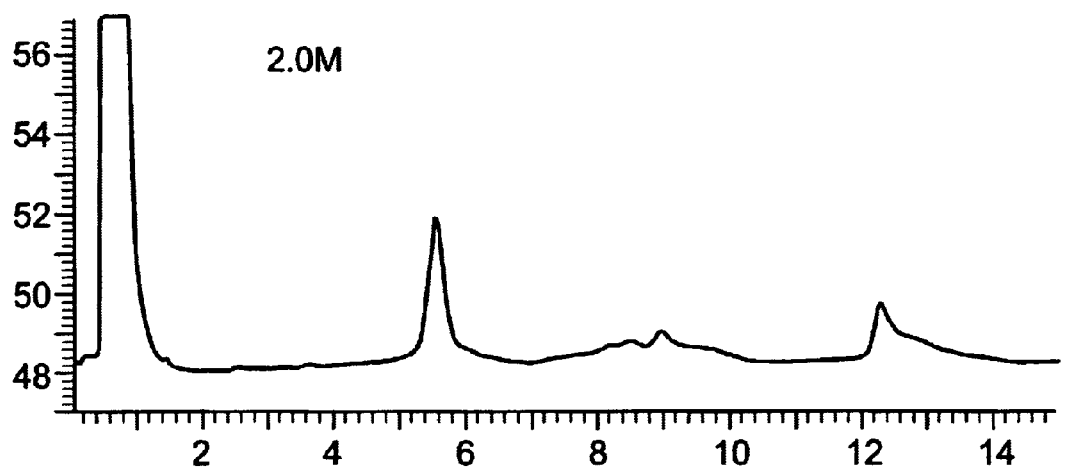
Figure 6B:
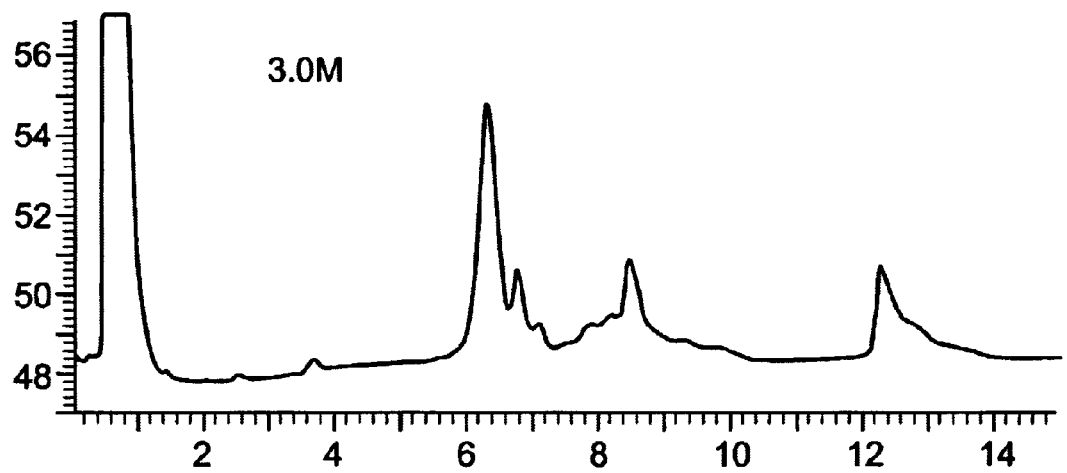
Figure 6C:
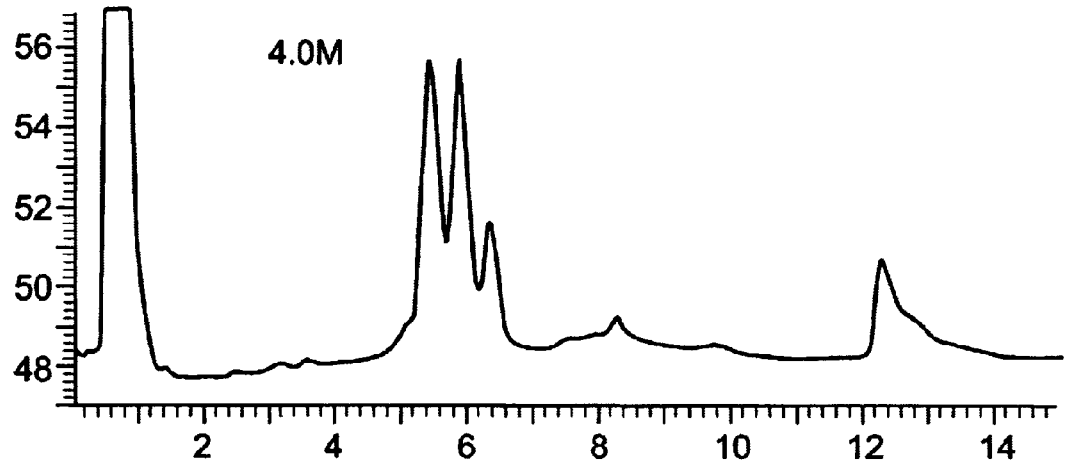

FIG. 6 shows human endostatin refold products under varying urea concentrations RP-HPLC tracings of human endostatin refold products at 3.0, 3.5, and 4.0 M urea at pH 7.5.

Figure 7:
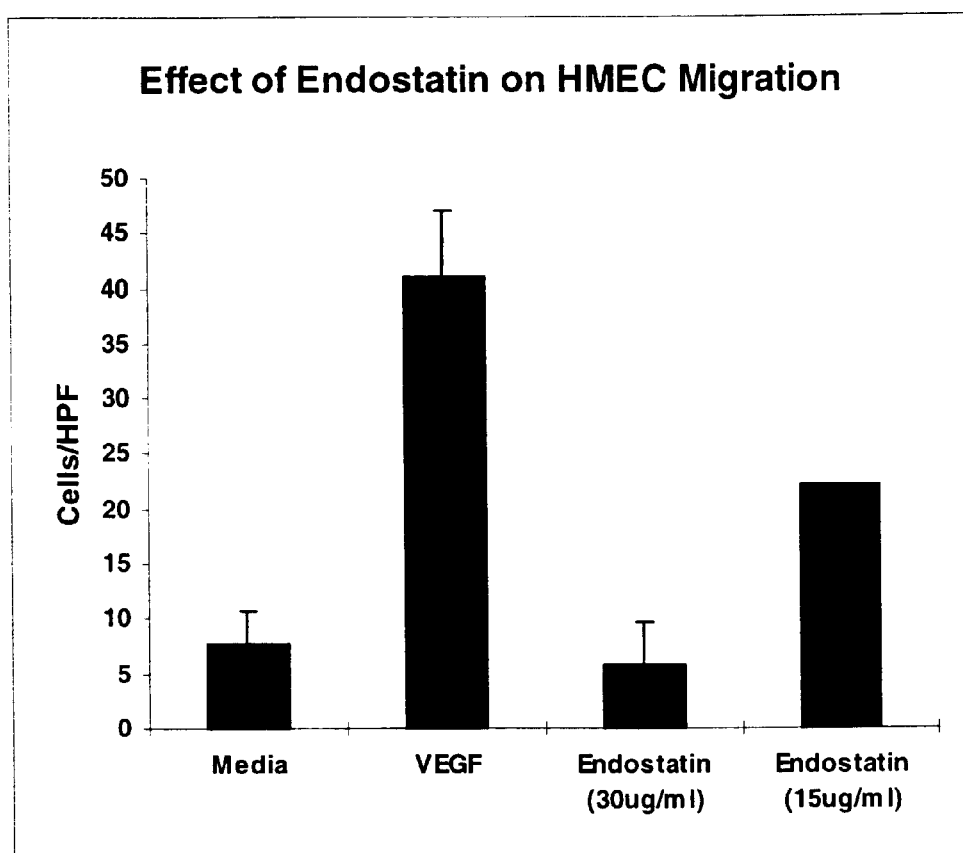

FIG. 7 shows the inhibition of HMEC migration by mouse endostatin

Purified mouse endostatin assayed in the HMEC cell migration assay at 15 and 30 ug/ml. Inhibition of migration was observed at both concentrations.

Figure 8:
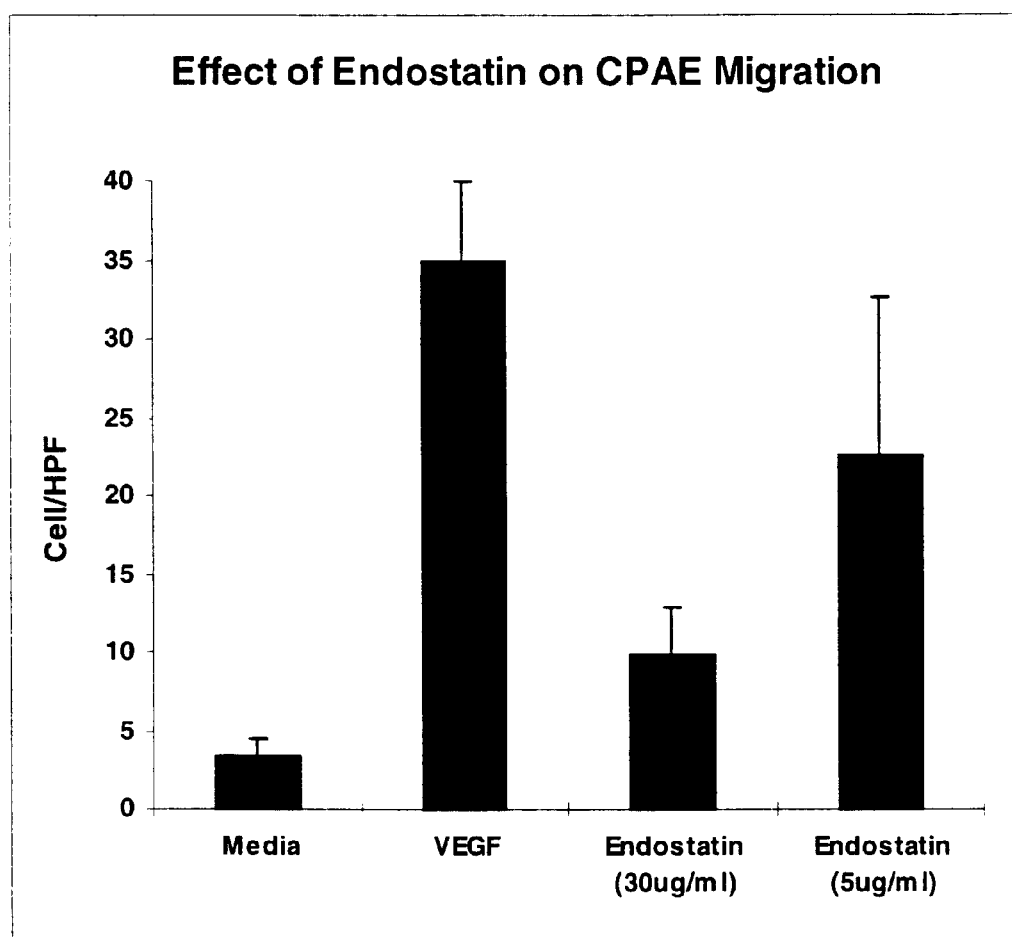

FIG. 8 shows the inhibition of CPAE migration by mouse endostatin

Purified mouse endostatin was assayed for inhibition of CPAE migration at 5 and 30 ug/ml. Inhibition of migration was observed at both concentrations.

Figure 9:
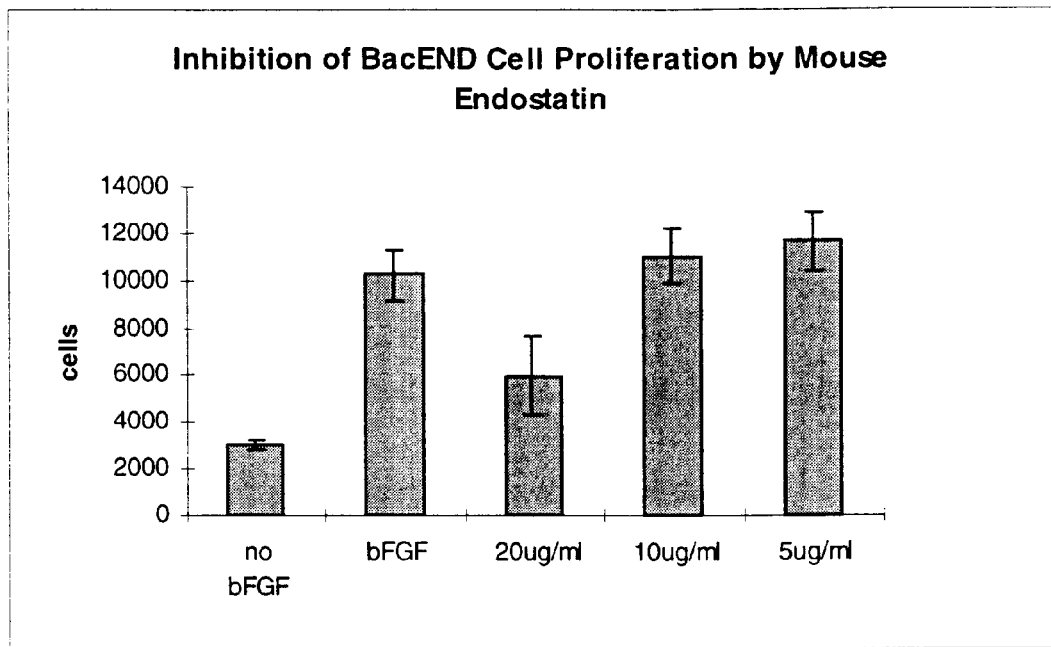

FIG. 9 shows the inhibition of endothelial cell proliferation by mouse endostatin.

Inhibition of endothelial cell proliferation by mouse endostatin. Significant inhibition was observed at 20 ug/ml.

Figure 10:
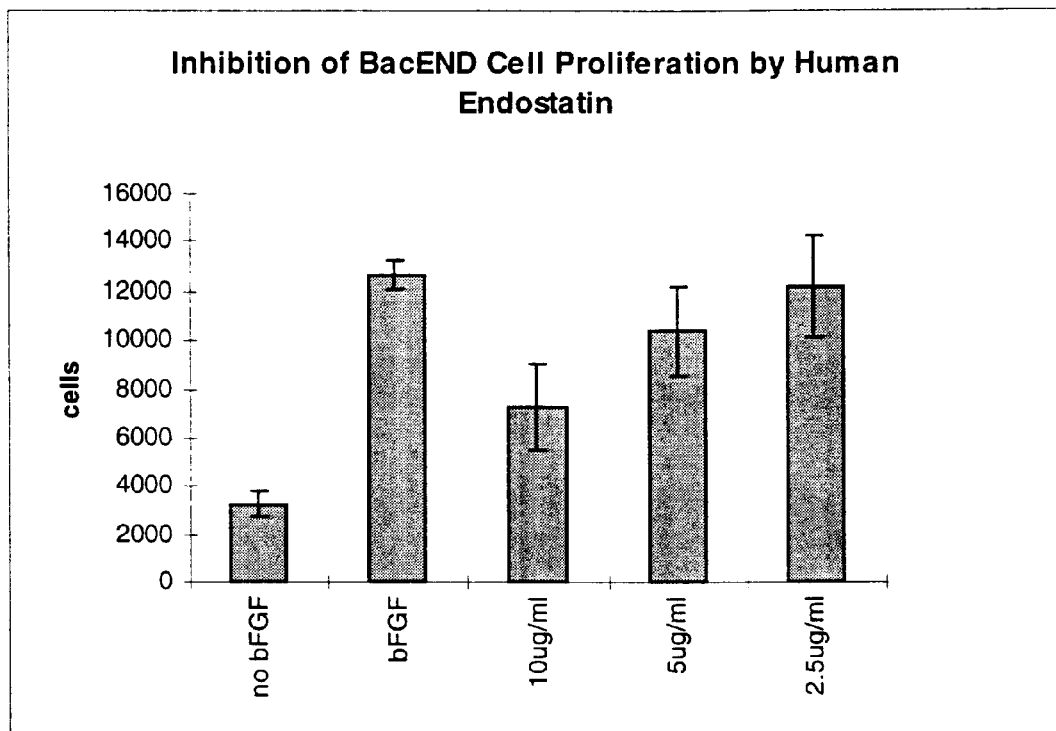

FIG. 10 shows the inhibition of endothelial cell proliferation by human endostatin.

Inhibition of endothelial cell proliferation by human endostatin. Significant inhibition was observed at 10 ug/ml of endostatin.

DETAILED DESCRIPTION OF THE INVENTION

The following examples will illustrate the invention in greater detail, although it will be understood that the invention is not limited to these specific examples. Various other examples will be apparent to the person skilled in the art after reading the present disclosure without departing from the spirit and scope of the invention. It is intended that all such other examples be included within the scope of the appended claims.

General Methods

General methods of cloning, expressing, and characterizing proteins are found in T. Maniatis, et al., *Molecular Cloning, A Laboratory Manual*, Cold Spring Harbor Laboratory, 1982, and references cited therein, incorporated herein by reference; and in J. Sambrook, et al., *Molecular Cloning, A Laboratory Manual*, 2$^{nd}$ edition, Cold Spring Harbor Laboratory, 1989, and references cited therein, incorporated herein by reference.

Unless noted otherwise, all specialty chemicals were obtained from Sigma, Co. (St. Louis, Mo.). Restriction endonucleases and T4 DNA ligase were obtained from New England Biolabs (Beverly, Mass.) or Boehringer Mannheim (Indianapolis, Ind.) or Promega (Madison, Wis.).

Strains and Plasmids

The bacterial strains used in these studies are listed in Table 1. Plasmids used in or constructed for this study are listed in Table 2.

Transformation of E. coli Strains

*E. coli* strains (Table 1), such as DH5 alpha and DH10B (Life Technologies, Rockville, Md.), and TG1 (Amersham Corp., Arlington Heights, Ill.) are used for transformation of ligation reactions and are the hosts used to prepare plasmid DNA for transfecting mammalian cells. *E. coli* strains, such as JM101 (Yanisch-Perron et al., *Gene*, 33: 103–119, 1985) and MON105 (Obukowicz, et al., *Appl. and Envir. Micr.*, 58: 1511–1523, 1992) can be used for expressing the proteins of the present invention in the cytoplasm or periplasmic space.

DH5 alpha and DH10B subcloning efficiency cells are purchased as competent cells and are ready for transformation using the manufacturer's protocol. *E. coli* strains JM101 AND MON105 are rendered competent to take up DNA using a $CaCl_2$ method. Typically, 20 to 50 mL of cells are grown in LB medium (1% Bacto-tryptone, 0.5% Bacto-yeast extract, 150 mM NaCl) to a density of approximately 1.0 absorbance unit at 600 nanometers (OD600) as measured by a Baush & Lomb Spectronic spectrophotometer (Rochester, N.Y.). The cells are collected by centrifugation and resuspended in one-fifth culture volume of $CaCl_2$ solution [50 mM $CaCl_2$, 10 mM Tris-Cl ((10 mM 2-amino-2-(hydroxymethyl) 1,3-propanediol hydrochloride, pH7.41] and are held at 4° C. for 30 minutes. The cells are again collected by centrifugation and resuspended in one-tenth culture volume of $CaCl_2$ solution. Ligated DNA is added to 0.2 mL of these cells, and the samples are held at 4° C. for 30–60 minutes. The samples are shifted to 42° C. for two minutes and 1.0 mL of LB is added prior to shaking the samples at 37° C. for one hour. Cells from these samples are spread on plates (LB medium plus 1.5% Bacto-agar) containing either ampicillin (100 micrograms/mL, ug/mL) when selecting for ampicillin-resistant transformants, or spectinomycin (75 ug/mL) when selecting for spectinomycin-resistant transformants. The plates are incubated overnight at 37° C.

Colonies are picked and inoculated into LB plus appropriate antibiotic (100 ug/mL ampicillin or 75 ug/mL spectinomycin) and are grown at 37° C. while shaking.

DNA Isolation and Characterization

Plasmid DNA can be isolated by a number of different methods and using commercially available kits known to those skilled in the art. Plasmid DNA is isolated using the Promega Wizard™ Miniprep kit (Madison, Wis.), the Qiagen QIAwell Plasmid isolation kits (Chatsworth, Calif.) or Qiagen Plasmid Midi or Mini kit. These kits follow the same general procedure for plasmid DNA isolation. Briefly, cells are pelleted by centrifugation (5000×g), the plasmid DNA released with sequential NaOH/acid treatment, and cellular debris is removed by centrifugation (10000×g). The supernatant (containing the plasmid DNA) is loaded onto a column containing a DNA-binding resin, the column is washed, and plasmid DNA eluted. After screening for the colonies with the plasmid of interest, the *E. coli* cells are inoculated into 50–100 ml of LB plus appropriate antibiotic for overnight growth at 37° C. in an air incubator while shaking. The purified plasmid DNA is used for DNA sequencing, further restriction enzyme digestion, additional subcloning of DNA fragments and transfection into *E. coli*, mammalian cells, or other cell types.

Sequence Confirmation

Purified plasmid DNA is resuspended in deionized $H_2O$ and its concentration is determined by measuring the absorbance at 260/280 nm in a Bausch and Lomb Spectronic 601 UV spectrometer. DNA samples are sequenced using ABI PRISM™ DyeDeoxy™ terminator sequencing chemistry (Applied Biosystems Division of Perkin Elmer Corporation, Lincoln City, Calif.) kits (Part Number 401388 or 402078) according to the manufacturer's suggested protocol, usually modified by the addition of 5% DMSO to the sequencing mixture. Sequencing reactions are performed in a DNA thermal cycler (Perkin Elmer Corporation, Norwalk, Conn.) following the recommended amplification conditions. Samples are purified to remove excess dye terminators with Centri-Sep™ spin columns (Princeton Separations, Adelphia, N.J.) and lyophilized. Fluorescent dye labeled sequencing reactions are resuspended in deionized formamide, and sequenced on denaturing 4.75% polyacrylamide-8M urea gels using ABI Model 373A and Model 377 automated DNA sequencers. Overlapping DNA sequence fragments are analyzed and assembled into master DNA contigs using Sequencher DNA analysis software (Gene Codes Corporation, Ann Arbor, Mich.).

Small-scale Expression of Endostatin in E. coli

*E. coli* strain MON105 or JM101 harboring the plasmid of interest is grown at 37° C. in M9 plus casamino acids medium with shaking in an air incubator Model G25 from New Brunswick Scientific (Edison, N.J.). Growth is monitored at $OD_{600}$ until it reaches a value of 1.0, at which time nalidixic acid (10 mg/mL) in 0.1 N NaOH is added to a final concentration of 50 μg/mL. The cultures are then shaken at 37° C. for three to four additional hours. A high degree of aeration is maintained throughout the culture period in order to achieve maximal production of the desired gene product. The cells are examined under a light microscope for the presence of inclusion bodies (IB). One mL aliquots of the culture are removed for analysis of protein content by boiling the pelleted cells, treating them with reducing buffer and electrophoresis via SDS-PAGE (see Maniatis et al., "Molecular Cloning: A Laboratory Manual", 1982). The culture is centrifuged (5000×g) to pellet the cells.

Large (10L)-scale Expression of Endostatin in E. coli

The Endostatin molecules were all scaled up in a 10 L Biostat E™ fermenter (B. Braun Biotech Inc., Allentown Pa.). The fermentation medium used was M9 salts supplemented with 2% casamino acids (Difco Laboratories, Detroit Mich.) and glucose. Approximately one milliliter of a thawed culture was transferred to a 3.8 L Fernbach shake flask containing 1.0 L of medium and then incubated at 37° C. at a shaker speed of 250 rpm for 12 hours. This shake flask culture was then used to inoculate a 10 L fermenter containing 9.0 L of medium. The fermentation conditions were as follows: agitation=1000 rpm, sparger airflow rate= 15 liters/min, pH control=7.0 by the addition of $NH_4OH$, backpressure=10 psi, dissolved oxygen control >30%, and temperature=37° C. Glucose was initially batched in at 15 g/l and controlled at 2–5 g/l by the addition of a 50% glucose feed stock. The fermentation culture was grown to an initial OD (550 nm)=12–15 and induced with 50 mg/l nalidixic acid. The fermentation was harvested four hours post induction by continuous-flow centrifugation.

10L Scale Inclusion Body Isolation

The cell paste from a 10L fermentation was resuspended in approximately 6.0 L of 50 mM Tris/ 150 mM EDTA buffer. The resuspension was passed once through a microfluidizer® (Newton, Mass.) at 10,000 psi and temperature maintained under 8° C. The recovered homogenate was then spun at 15,000×G for 25 minutes and mixed to consistency with an Ultr-Turrax mixer. The cell paste resuspension was then homogenized by passing the cell suspension two times through a Microfluidizer™ (Newton, Mass.) operating at 10,000 psi pressure. The temperature of the homogenate was maintained less than 6° C. by collection in a stainless steel container placed in an ice bath. Inclusion bodies were then isolated by centrifugation of the cell homogenate at 15,000×g for 30 minutes and removal of supernatant. Inclusion bodies were then washed a total of two times by resuspending the inclusion bodies in chilled D.I. and centrifugation at 15,000×g for 30 minutes. Endostatin inclusion bodies were then frozen at −70° C.

Small-scale Isolation of Inclusion Bodies

The cell pellet from a 330 mL E. coli culture is resuspended in 15 mL of sonication buffer (50 mM Tris-HCl, pH 8.0, 1 mM EDTA). These resuspended cells are sonicated using the microtip probe of a Sonicator Cell Disruptor (Model W-375, Heat Systems-Ultrasonics, Inc., Farmingdale, N.Y.). Three rounds of sonication in sonication buffer followed by centrifugation are employed to disrupt the cells and wash the inclusion bodies (IB). The first round of sonication is a 3 minute burst followed by a 1 minute burst, and the final two rounds of sonication are for 1 minute each.

Extraction and Refolding of Human and Mouse Proteins From Inclusion Body Pellets All steps are at 4° C. Mouse endostatin inclusion bodies were dissolved in 6M urea, 5 mM DTT, 50 mM Bis-Tris Propane, pH 10.8 at 2.5 mg/ml endostatin. This solution was stirred for 2 hours and followed by addition of cystine (stock 0.2 M, pH 10.5) to 10 mM. This was mixed for 5 minutes and then diluted to 0.25 mg/ml endostatin in 3.5 M urea, 100 mM Bis-Tris propane, pH 7.0. It was then stirred for 60 hours to complete the refolding of the protein as assessed by reverse-phase HPLC.

Human endostatin inclusion bodies were dissolved in 10 mM cysteine, 6M urea, 50 mM Bis-Tris propane, pH 10.8, at 2.5 mg/ml endostatin. This was stirred for 2 hours followed by addition of 10 mM cystine (stock 0.2 M, pH 10.5) and mixed for 5 minutes. This solution was then diluted to 0.25 mg/ml endostatin in 3.0 M urea, 100 mM Bis-Tris propane, pH 7.5 and stirred for 60 hours to complete the refolding step.

Purification

Purification of mouse or human endostatin was achieved using the same process using acid precipitation followed by column chromatography on a sulfo-propyl-column. The refolded sample was concentrated approximately 10-fold by ultrafiltration and the pH lowered to pH 5.0 with acetic acid. This was then dialyzed extensively against 5 mM acetic acid, pH 5.0. The precipitate was removed by filtration and the filtrate applied to a Pharmacia S-Sepharose HP column. The column was washed with 1 column volume of equilibrating buffer and the protein eluted using a 20 column volume gradient of 50 mM phosphate, pH 6.5 to the same buffer containing 0.4 M NaCl. Fractions were analyzed by SDS-gel electrophoresis and RP-HPLC and pooled and dialyzed against PBS and frozen.

In some cases the folded proteins can be affinity-purified using affinity reagents such as monoclonal antibodies or receptor subunits attached to a suitable matrix. Purification can also be accomplished using any of a variety of chromatographic methods such as: ion exchange, gel filtration or hydrophobic interaction chromatography or reversed phase HPLC. These and other protein purification methods are described in detail in Methods in Enzymology, Volume 182 "Guide to Protein Purification," edited by Murray Deutscher, Academic Press, San Diego, Calif., 1990.

Protein Characterization

The purified protein is analyzed by RP-HPLC, electrospray mass spectrometry, amino acid sequencing and SDS-PAGE. The protein quantitation is done by amino acid composition, RP-HPLC, and Bradford protein determination. In some cases tryptic peptide mapping is performed in conjunction with electrospray mass spectrometry to confirm the identity of the protein.

Endothelial Cell Proliferation Assay

The endothelial cell proliferation assay was performed as described by Cao et al. (*J. Biol. Chem.* 271: 29461–29467, 1996). Briefly, human dermal microvascular endothelial cells (HdMVEC, Clonetics) or bovine adrenal cortex microvascular endothelial cells (BacEnd, Incell, San Antonio, Tx.) were maintained in MCDB131 containing 5% heat-inactivated fetal bovine serum (FBS, Hyclone), antibiotics, 100 ug/ml heparin (Sigma) and 100 ug/ml endothelial mitogen (Biomedical Technologies). Confluent monolayers at passages 2–5 were dispersed in 0.05% trypsin and resuspended in complete medium. Five hundred ul of complete media containing $1.25 \times 10^4$ cells were seeded into wells of a 24-well tissue culture plate coated with 0.1% gelatin (Sigma). The cells were incubated overnight at 37° C./5% $CO_2$ at which time the media was replaced with 250 ul of media containing 5% FBS and various concentrations of inhibitors. After 30 minutes of incubation, 250 ul of media containing 1 ng/ml bFGF (R&D Systems) was added and the cells were incubated for an additional 72 hours, at which time they were trypsinized and counted with a Coulter counter.

Endothelial Cell Migration Assay

The endothelial cell migration assay is performed essentially as previously described (Gately et al., *Cancer Res.* 56:4887–4890, 1996). To determine the ability of endostatin to inhibit the migration of endothelial cells, migration assays were performed in a transwell chamber (Costar) containing 8 mm pore size polycarbonate membranes. The cells utilized in the assay were either human microvascular endothelial cells (Emory University, Atlanta, Ga.) or bovine pulmonary artery endothelial cells (Monsanto, St. Louis, Mo.). The cells were starved overnight before use in MCDB131+0.1% BSA (human cells) or DMEM+0.1%BSA (bovine cells), harvested, and resuspended in the same media at $10^6$ cells/ml. The lower side of the transwells were coated with 0.1% gelatin for 30 minutes at 37° C. before addition of $2\times10^5$ cells to the upper chamber. The transwell was moved to a well containing the chemoattractant (bFGF or VEGF) in the lower chamber. Migration was allowed to occur overnight at 37° C. The membranes were then fixed and stained, and the number of cells that migrated to the lower side of the membrane counted in 3 high powered fields.

EXAMPLE 1

Construction of pMON24345 (SEQ ID NO: 8) and Selection of Strains Producing High Levels of Mouse Endostatin Total mouse RNA (Clontech Laboratories Inc, Palo Alto, Calif.), 5 ug, was mixed with 500 ng of random hexamer primer (Promega Corporation, Madison, Wis.), heated for 10 min at 65° C., then cooled for 2 min on ice. To the RNA/primer mixture was added 20 units of Rnasin (Promega), SuperScript II buffer, DTT to a final concentration of 0.01 M, dNTP mix (Boehringer) to a final concentration of 0.005 M and 200 units of SuperScript II transcriptase (Life Technologies Inc.). The reaction was incubated at 42° C. for 1.5 hours and the enzyme was inactivated by incubating the reaction at 70° C. for 5 min. RNA was removed by adding 2 units of E. coli RNase H (Life Technologies Inc.) and incubating the reaction at 37° C. for 20 min. Double-stranded DNA was generated by polymerase chain reaction with the addition of dNTPs to a final concentration of 1.6 mM, 50 pmol of 5 prime mouse endostatin primer (SEQ ID NO: 1), 50 pmol of 3 prime mouse endostatin primer (SEQ ID NO: 2), High Fidelity PCR buffer, and 2.5 units of High-Fidelity enzyme (Boehringer). The reaction mixture was incubated at 95° C. for 3 min, then cycled 10 times through a 15 second 94° C. incubation, a 30 second 50° C. incubation, a 4 min. 72° C. incubation, then cycled 15 times through a 15 second 94° C. incubation, 30 second 50° C. incubation, 4 min plus 20 second extension per cycle 72° C. incubation. Finally the reaction was incubated at 72° C. for 7 min.

Double-stranded DNA was subcloned into the pCRII vector (Invitrogen) by adding 1 ul of the PCR reaction to 25 ng of vector, 1 unit of T4 ligase in the ligation buffer. The ligase reaction was incubated at 12° C. overnight. The ligated DNA was transformed into DH5 alpha competent cells (Life Technologies Inc., Rockville, Md.) and grown on LB amp plates. Two isolates with inserts as determined by EcoRI digestion were further characterized. The cDNA inserts of the two isolates, pMON24342 (SEQ ID NO: 5) and pMON24343 (SEQ ID NO: 6), were analyzed by DNA sequencing using standard dideoxy technology. To construct the correct coding DNA sequence both pMON24342 and pMON24343 were digested with ApaI. The ApaI mouse endostatin DNA fragment and the pMON24342 vector plus 5 prime mouse endostatin coding DNA sequence were isolated using the Qiaex II Gel Extraction Kit (Qiagen, Germany). The fragments were ligated together in 50 mM Tris-HCl pH 7.5, 10 mM $MgCl_2$, 50 ug/ml BSA and 1 unit T4 ligase. The reconstructed plasmid was transformed into DH5 alpha competent cells to generated pMON24344 (SEQ ID NO: 7). The plasmid pMON24344 was digested with NcoI and HindIII and the fragment isolated with Qiaex II Gel Extraction Kit. The pMON24344 NcoI/HindIII fragment with ligated into a NcoI/HindIII-digested dephosphorylated pMON5723 E. coli expression vector in 50 mM tris pH 7.5, 10 mM $MgCl_2$, 50 ug/ml BSA and 1 unit of T4 ligase. The ligated DNA was transformed into MON105 and isolates selected on Spec LB plates to generate pMON24345 (SEQ ID NO: 8). E. coli strain MON105 harboring pMON24345 was induced with 10 mg/ml nalidixic acid and mouse endostatin expressed in these cells was monitored by SDS-PAGE.

EXAMPLE 2

Construction of pMON 20440 (SEQ ID NO: 9) Encoding Human Endostatin

Total human RNA (Clontech Laboratories Inc, Palo Alto, Calif.), 5 ug, was mixed with 500 ng of random hexamer primer, heated for 10 min at 65° C. then cooled for 2 min on ice. To the RNA/primer mixture was added 20 units of Rnasin (Promega), SuperScript II buffer, DTT to a final concentration of 0.01 M, dNTP mix (Boehringer) to a final concentration of 0.005 M and 20 units of SuperScript II transcriptase. The reaction was incubated at 42° C. for 1.5 hours and the enzyme was inactivated by incubating the reaction at 70° C. for 5 min. RNA was removed by adding 2 units of E. coli RNase H and incubating the reaction at 37° C. for 20 min. Double-stranded DNA was generated by polymerase chain reaction with the addition of dNTPs to a final concentration of 1.6 mM, 50 pmol of 5 prime human endostatin primer (SEQ ID NO: 3), 50 pmol of 3 prime human primer (SEQ ID NO: 4), High-Fidelity PCR buffer, and 2.5 units of High-Fidelity enzyme (Boehringer). The reaction mixture was incubated at 95° C. for 3 min, then cycled 10 times through a 15 second 94° C. incubation, a 30 second 50° C. incubation, a 4 min 72° C. incubation, then cycled 15 times through a 15 second 94° C. incubation, 30 second 50° C. incubation, 4 min plus 20 second extension per cycle 72° C. incubation. Finally the reaction was incubated at 72° C. for 7 min.

The double stranded DNA was digested with NcoI and HindIII and ligated into a NcoI/HindIII digested dephosphorylated pMON2341 E. coli expression vector in 50 mM Tris-HCl pH 7.5, 10 mM $MgCl_2$, 50 ug/ml BSA and 1 unit of T4 ligase. The ligated DNA was transformed into E. coli strain MON105 and isolates selected on Amp LB plates to generate pMON20440 (SEQ ID NO: 9). E. coli strain MON105 harboring pMON20440 was induced with 10 mg/ml nalidixic acid and human endostatin expressed in these cells was monitored by SDS-PAGE.

EXAMPLE 3

Method for Refolding Mouse Endostatin

All steps are at 4° C. Mouse endostatin inclusion bodies were dissolved in 6 M urea, 5 mM DTT, 50 mM Bis-Tris Propane, pH 10.8 at 2.5 mg/ml. This solution was stirred for 2 hours and followed by addition of cystine (stock 0.2 M, pH 10.5) to 10 mM. This was mixed for 5 minutes and then diluted to 0.25 mg/ml endostatin in 3.5 M urea, 100 mM Bis-Tris propane, pH 7.0. It was then stirred for 60 hours to complete the refolding of the protein as assessed by reverse-phase HPLC. Other pH conditions and urea concentrations can be used, but at lower efficiency. FIGS. 3 and 4 show HPLC tracings of mouse endostatin refold products under varying pH conditions and urea concentrations, respectively. FIGS. 7, 8, and 9 show inhibitory activity of purified mouse endostatin in endothelial cell proliferation and cell migration assays.

EXAMPLE 4

Method for Refolding Human Endostatin

All steps are at 4° C. Human endostatin inclusion bodies were dissolved in 10 mM cysteine, 6 M urea, 50 mM Bis-Tris propane, pH 10.8, at 2.5 mg/ml endostatin. This was stirred for 2 hours followed by addition of 10 mM cystine (stock 0.2 M, pH 10.5) and mixed for 5 minutes. This solution was then diluted to 0.25 mg/ml endostatin in 3.0 M urea, 100 mM Bis-Tris propane, pH 7.5 and stirred for 60 hours to complete the refolding step. Other pH conditions and urea concentrations can be used, but at lower efficiency. FIGS. 5 and 6 show HPLC tracings of human endostatin refold products under varying pH conditions and urea concentrations, respectively. FIG. 10 shows inhibitory activity of purified human endostatin in an endothelial cell proliferation assay.

Those skilled in the art will recognize that the solubilization, refolding, and purification conditions outlined above represent dramatic improvements over published methods for purifying endostatin from bacteria. Production of endostatin on a commercial scale for use in preclinical studies and clinical trials will require vast amounts of soluble properly-refolded material which possesses the desired biological characteristics. Commercial development of endostatin as a therapeutic product requires thoroughly-characterized material that behaves the same in all applications. Soluble, properly-refolded endostatin, therefore, is more desirable than suspensions of insoluble material for in vitro assays and for in vivo studies of the effectiveness, potency, pharmacokinetics, and pharmacodynamics of this protein. The dramatically-improved process for expressing, solubilizing, refolding, purifying, and characterizing this material outlined in this disclosure will greatly facilitate subsequent studies aimed at developing endostatin, endostatin-fragments, muteins, insulteins, permuteins, or chimeras thereof, or conjugates of these with other anti-angiogenic proteins or small molecules which are useful as compounds in the treatment of angiogenesis disorders, including cancer.

All references, patents, or applications cited herein are incorporated by reference in their entirety, as if written herein.

TABLES

TABLE 1

| | Strains | |
|---|---|---|
| Designation | Description or Genotype | Reference/Source |
| DH5α ™ | F−, phi80 dlacZdeltaM15, delta(lacZYA-argF)U169, deoR, recA1, endA1, hsdR17 (rk−, mk+), phoA, supE44, lambda-, thi-1, gyrA96, relA1 | Life Technologies, Rockville, Maryland |
| DH10B | F−mcrA Δ(mrr-hsdRMS-mcrBC) φdlacZΔM15 ΔlacX74 deoR recA1 endA1 araD139 Δ(ara, leu)7697 galU galKλ rpsL nupG | Life Technologies, Rockville, Maryland |
| JM101 (ATCC # 33876) | delta (pro lac), supE, thi, F'(traD36, proA+B+, lacI$^q$ lacZdeltaM15) | Yanisch-Perron, et al., Gene, 33:103–119, 1985 |
| MON105 (ATCC # 55204) | F−, lambda-,IN (rrnD, rrnE)1, rpoD+, rpoH358 | Obukowicz, et al., Appl. and Envir. Micr., 58:1511–1523, 1992 |
| TG1 | delta(lac-pro), supE, thi-1, hsdD5/F'(traD36, proA+B+, lacI$^q$ lacZdeltaM15) | Amersham Corp., Arlington Heights, Illinois |

TABLE 2

| | | Plasmids | | |
|---|---|---|---|---|
| Plasmid | SEQ ID NO. | Marker | Description | Source |
| pMON2341 | | Amp$^R$ | Generic Amp-resistant *E. coli* expression vector containing the *E. coli* recA1 promoter and G10L ribosome binding site, chloramphenicol acetyl transferase gene (cat3) gene and ori M13 | Lab collection |
| pMON5723 | | Spec$^R$ | Generic Spec-resistant *E. coli* expression vector containing the *E. coli* recA1 promoter and G10L ribosome binding site | (Olins and Rangwala, Methods Enzymol. 185 (Gene Expression Technol.): 115–119, 1990) |
| pCRII | | Amp$^R$ | Commercial PCR fragment (TA) cloning vector | Invitrogen |
| pMON24342 | #5 | Amp$^R$ | pCR II (TA) cloning vector + PCR fragment encoding mouse endostatin, including the native mouse collagen XVIII C-terminal region. EcoRI fragment in pCRII (Amino acids 1104–1288) | This work |
| pMON24343 | #6 | Amp$^R$ | pCR II (TA) cloning vector + PCR fragment encoding mouse endostatin, including the native mouse collagen XVIII C-terminal region. EcoRI fragment in pCRII (Amino acids 1104–1288) | This work |
| pMON24344 | #7 | Amp$^R$ | pCR II (TA) cloning vector + PCR fragment encoding mouse endostatin, including the native mouse collagen XVIII C-terminal region. EcoRI fragment in pCRII (Amino acids 1104–1288) | This work |
| pMON24345 | #8 | Spec$^R$ | pMON5723 NcoI/HindIII + NcoI/HindIII fragment of mouse endostatin, including the native mouse collagen XVIII C-terminal region (Amino acids 1104–1288) | This work |
| pMON20440 | #9 | Spec$^R$ | pMON2341 NcoI/HindIII + NcoI/HindIII encoding human endostatin, including the native human collagen XVIII C-terminal region | This work |

TABLE 3

SEQ ID Correlation Table

| SEQ ID NO: | Sequence | Description |
| --- | --- | --- |
| 1 | gcgcgcccatggctcatactcatcaggac; | 5 prime PCR primer for mouse endostatin |
| 2 | gcgcgcaagcttattatttggagaaagaggtcatgaag; | 3 prime PCR primer for mouse endostatin |
| 3 | GCGCGCCCAT GGCTCACAGC CACCGCGACT TCCAGCCGGT GCTCCACCTG GTTGCGCTCA ACAGCCCCCT G; | 5 prime PCR primer for human endostatin |
| 4 | GCGCGCAAGC TTATTACTTG GAGGCAGTCA TGAAGCTGTT CTCAATGCAG AGCACGATGT AGGCGTGATG GCAGCTCGC; | 3 prime PCR primer for human endostatin |
| 5 | | pMON42342 EcoR1 insert encoding mouse endostatin |
| 6 | | pMON42343 EcoR1 insert encoding mouse endostatin |
| 7 | | pMON42344 EcoR1 insert encoding mouse endostatin |
| 8 | | pMON42345 EcoR1 insert encoding mouse endostatin |
| 9 | | pMON20440 encoding human endostatin |
| 10 | AHTHQDFQPVLHLVALNTPLSGGMRGIRGADFQCFQQARA VGLSGTFRAFLSS RLQDLYSIVRRADRGSVPIVNLKDEVLSPSWDSLFSGSQG QLQPGARIFSFDGRDV LRHPAWPQKSVWHGSDPSGRRLMESYCETWRTETTGATGQ ASSLLSGRLLEQK AASCHNSYIVLCIENSFMTSFSK; | Mouse Endostatin Amino Acid Sequence |
| 11 | AHSHRDFQPVLHLVALNSPLSGGMRGIRGADFQCFQQARA VGLAGTFRAFLSS RLQDLYSIVRRADRAAVPIVNLKDELLFPSWEALFSGSEG PLKPGARIFSFDGKDV LRHPTWPQKSVWHGSDPNGRRLTESYCETWRTEAPSATGQ ASSLLGGRLLGQS AASCHHAYIVLCIENSFMTA—SK; | Human Endostatin Amino Acid Sequence |

---

What is claimed is:

1. A method of producing endostatin comprising the steps of:

(a) transforming a prokaryotic host cell with an expression vector comprising an isolated polynucleotide encoding endostatin;

(b) culturing said prokaryotic host cells under conditions suitable for production of inclusion bodies containing endostatin;

(c) recovering said inclusion bodies;

(d) solubilizing the endostatin in said inclusion bodies at an elevated pH in the presence of a denaturant;

(e) properly refolding the endostatin at about neutral pH; and (f) isolating properly folded, active forms of endostatin; wherein said elevated pH is from pH 9 to about pH 11.5;

wherein said near neutral pH is from pH 6 to about pH 8.5;

wherein the denaturant is urea at a concentration of from about 4 M to about 10 M during said solubilization step, and urea is present at a concentration of from about 2 M to about 4 M during said refolding step; and wherein the refolding is carried out in the presence of a reducing agent that reduces disulfide linkages to sulfhydryl groups, wherein said reducing agent is selected from the group consisting of dithiothreitol (DTT), present at a concentration of about 0.5 to about 2 mM, and cysteine, present at a concentration of about 0.5 mM to about 4 mM; and wherein the concentration of the endostatin gene product in the refolding step is from about 0.2 to about 2 mg/ml.

2. The method of claim 1 wherein said elevated pH is from about pH 10 to about pH 11.

3. The method of claim 2 wherein said elevated pH is about pH 10.5.

4. The method of claim 1 wherein said near-neutral pH in the refolding step is from about pH 7.0 to about pH 8.0.

5. The method of claim 4 wherein said near-neutral pH in the refolding step is about pH 7.5.

6. The method of claim 1 wherein urea is present at a concentration of about 6 M during said solubilization step.

7. The method of claim 1 wherein urea is present at a concentration of about 3.5 M during said refolding step.

8. The method of claim 1 wherein DTT is present at a concentration of from about 2 mM to about 10 mM during said solubilization step.

9. The method of claim 8 wherein DTT is present at a concentration of about 5 mM during said solubilization step.

10. The method of claim 1 wherein DTT is present at a concentration of about 0.5 mM during said refolding step.

11. The method of claim 1 wherein cysteine is present at a concentration of from about 5 mM to about 20 mM during said solubilization step.

12. The method of claim 11 wherein cysteine is present at a concentration of about 10 mM during said solubilization step.

13. The method of claim 1 wherein cysteine is present at a concentration of about 1 mM during said refolding step.

14. The method of claim 1 wherein disulfide bonds are formed through air oxidation during said refolding step.

15. The method of claim 14 wherein said air oxidation step is carried out from about 12 hours to about 96 hours.

16. The method of claim 15 wherein said air oxidation step is carried out from about 24 hours to about 72 hours.

17. The method of claim 16 wherein said air oxidation step is carried out for about 60 hours.

18. The method of claim 1 wherein said gene product is present at a concentration of from about 1 to about 20 mg/ml during said solubilization step.

19. The method of claim 18 wherein said gene product is present at a concentration of about 2.5 mg/ml during said solubilization step.

20. The method of claim 1 wherein said gene product is present at a concentration of about 0.25 mg/ml during said refolding step.

21. The method of claim 1 which further includes the step of purifying the endostatin by a process selected from the group consisting of ion-exchange chromatography, hydrophobic interaction chromatography and reversed phase-high performance liquid chromatography (RP-HPLC).

22. The method of claim 1 wherein said polynucleotide encodes mouse endostatin.

23. The method of claim 1 wherein said polynucleotide encoding endostatin is selected from the group consisting of SEQ ID NO: 5; SEQ ID NO: 6; SEQ ID NO: 7; and SEQ ID NO: 8.

24. The method of claim 1 wherein said polynucleotide encodes human endostatin.

25. The method of claim 1 wherein said polynucleotide encoding endostatin is SEQ ID NO: 9.

26. The method of claim 1 wherein said prokaryotic host cell is *E. coli*.

* * * * *

```
                          SEQUENCE LISTING

<160> NUMBER OF SEQ ID NOS: 13

<210> SEQ ID NO 1
<211> LENGTH: 29
<212> TYPE: DNA
<213> ORGANISM: human

<400> SEQUENCE: 1
gcgcgcccat ggctcatact catcaggac                                       29

<210> SEQ ID NO 2
<211> LENGTH: 38
<212> TYPE: DNA
<213> ORGANISM: human

<400> SEQUENCE: 2
gcgcgcaagc ttattatttg gagaaagagg tcatgaag                             38

<210> SEQ ID NO 3
<211> LENGTH: 71
<212> TYPE: DNA
<213> ORGANISM: human

<400> SEQUENCE: 3
gcgcgcccat ggctcacagc caccgcgact tccagccggt gctccacctg gttgcgctca    60
``` acagcccct g                                                              71

<210> SEQ ID NO 4
<211> LENGTH: 79
<212> TYPE: DNA
<213> ORGANISM: human

<400> SEQUENCE: 4
gcgcgcaagc ttattacttg gaggcagtca tgaagctgtt ctcaatgcag agcacgatgt        60
aggcgtgatg gcagctcgc                                                     79

<210> SEQ ID NO 5
<211> LENGTH: 620
<212> TYPE: DNA
<213> ORGANISM: human
<220> FEATURE:
<221> NAME/KEY: misc_feature
<222> LOCATION: (1)...(620)
<223> OTHER INFORMATION: n = A,T,C or G

<400> SEQUENCE: 5
gcgcgcccat ggctcatact catcaggact ttcagccagt gctccacctg gtggcactga        60
acacccccct gtctggaggc atgcgtggta ccgtggagc agatttccag tgcttccagc        120
aagcccgagc cgtggggctg tcgggcacct tccgggcttt cctgtcctct aggctgcagg       180
atctctatag catcgtgcgc cgtgctgacc ggggtctgt gcccatcgtc aacctgaagg        240
acgaggtgct atctcccagc tgggactccc tgttttctgg ctcccagggt caactgcaac       300
ccggggcccg catcttttct tttgacggca gagatgtcct gagacaccca gcctggccgc       360
agaagagcgt atggcacggc tcggacccca gtgggcggag gctgatggag agttactgtg       420
agacatggcg aactgaaact actggggcta caggtcaggc ctcctccctg ctgtcaggca       480
ggctcctgga acagaaagct gcgagctgcc acaacagcta catcgtcctg tgcattgaga       540
atagcttcat gacctctttc tcaagccgaa ttccagcaca ctggcgncgt tactagtgat       600
ccgagctcgt accaagttaa                                                   620

<210> SEQ ID NO 6
<211> LENGTH: 582
<212> TYPE: DNA
<213> ORGANISM: human

<400> SEQUENCE: 6
gcgcgcccat ggctcatact catcaggact ttcagccagt gctccacctg gtggcactga        60
acacccccct gtctggaggc atgcgtggta ccgtggagc aaatttccag tgcttccagc       120
aagcccgagc cgtggggctg tcgggcacct tccgggcttt cctgtcctct aggctgcagg       180
atctctatay catcgtgcgc cgtgctgacc ggggtctgt gcccatcgtc aacctgaagg        240
acgaggtgct atctcccagc tgggactccc tgttttctgg ctcccagggt caactgcaac       300
ccggggcccg catcttttct tttgacggca gagatgtcct gagacaccca gcctggccgc       360
agaagagcgt atggcacggc tcggacccca gtgggcggag gctgatggag agttactgtg       420
agacatggcg aactgaaact actggggcta caggtcaggc ctcctccctg ctgtcaggca       480
ggctcctgga acagaaagct gcgagctgcc acaacagcta catcgtcctg tgcattgaga       540
atagcttcat gacctctttc tccaaataat aagcttggcg cg                          582

<210> SEQ ID NO 7
<211> LENGTH: 580

-continued

```
<212> TYPE: DNA
<213> ORGANISM: human

<400> SEQUENCE: 7
gcgccccatg ctcatactca tcaggacttt cagccagtgc tccacctggt ggcactgaac    60
acccccctgt ctggaggcat gcgtggtatc cgtggagcag atttccagtg cttccagcaa   120
gcccgagccg tggggctgtc gggcaccttc cgggcttttc tgtcctctag gctgcaggat   180
ctctatagca tcgtgcgccg tgctgaccgg ggtctgtgc ccatcgtcaa cctgaaggac    240
gaggtgctat ctcccagctg gactccctg ttttctggct cccagggtca gtgcaaccc    300 ggggcccgca tcttttcttt tgacggcaga gatgtcctga cacccagc ctggccgcag    360 aagagcgtat ggcacggctc ggaccccagt gggcggaggc tgatggagag ttactgtgag   420
acatggcgaa ctgaaactac tggggctaca ggtcaggcct cctccctgct gtcaggcagg   480
ctcctggaac agaaagctgc gagctgccac aacagctaca tcgtcctgtg cattgagaat   540
agcttcatga cctctttctc caaataataa gcttgcgcgc                         580

<210> SEQ ID NO 8
<211> LENGTH: 568
<212> TYPE: DNA
<213> ORGANISM: human

<400> SEQUENCE: 8
catgctcata tcatcagga ctttcagcca gtgctccacc tggtggcact gaacacccccc   60 ctgtctggag gcatgcgtgg tatccgtgga gcagatttcc agtgcttcca gcaagcccga   120
gccgtggggc tgtcgggcac cttccgggct ttcctgtcct ctaggctgca ggatctctat   180
agcatcgtgc gccgtgctga ccggggtct gtgcccatcg tcaacctgaa ggacgaggtg    240
ctatctccca gctgggactc cctgttttct ggctcccagg gtcaagtgca acccggggcc   300
cgcatctttt cttttgacgg cagagatgtc ctgagacacc cagcctggcc gcagaagagc   360
gtatggcacg gctcggaccc cagtgggcgg aggctgatgg agagttactg tgagacatgg   420
cgaactgaaa ctactggggc tacaggtcag gcctcctccc tgctgtcagg caggctcctg   480
gaacagaaag ctgcgagctg ccacaacagc tacatcgtcc tgtgcattga gaatagcttc   540
atgacctctt tctccaaata taagctt                                      568

<210> SEQ ID NO 9
<211> LENGTH: 563
<212> TYPE: DNA
<213> ORGANISM: human

<400> SEQUENCE: 9
catggcacag ccaccgcgac ttccagccgg tgctccacct ggttgcgctc aacagccccc   60
tgtcaggcgg catgcggggc atccgcgggg ccgacttcca gtgcttccag caggcgcggg   120
ccgtggggct ggcgggcacc ttccgcgcct tcctgtcctc gcgcctgcag gacctgtaca   180
gcatcgtgcg ccgtgccgac cgcgcagccg tgcccatcgt caacctcaag gacgagctgc   240
tgtttcccag ctgggaggct ctgttctcag gctctgaggg tccgctgaag cccggggcac   300
gcatcttctc ctttgacggc aaggacgtcc tgaggcaccc cacctggccc cagaagagcg   360
tgtggcatgg ctcggacccc aacgggcgca ggctgaccga gagctactgt gagacgtggc   420
ggacggaggc tccctcggcc acgggccagg cctcctcgct gctgggggc aggctcctgg    480 ggcagagtgc cgcgagctgc catcacgcct acatcgtgct ctgcattgag aacagcttca   540
```
tgactgcctc caagtaataa gct                                                  563

<210> SEQ ID NO 10
<211> LENGTH: 124
<212> TYPE: PRT
<213> ORGANISM: human

<400> SEQUENCE: 10

Ala His Thr His Asp Val His Val Ala Asn Thr Ser Gly Gly Met Arg
1               5                   10                  15

Gly Arg Gly Ala Asp Cys Ala Arg Ala Val Gly Ser Gly Thr Arg Ala
            20                  25                  30

Ser Ser Arg Asp Tyr Ser Val Arg Arg Ala Asp Arg Gly Ser Val Val
        35                  40                  45

Asn Lys Asp Val Ser Ser Trp Asp Ser Ser Gly Ser Gly Ala Arg
    50                  55                  60

Ser Asp Gly Arg Asp Val Arg His Ala Trp Lys Ser Val Trp His Gly
65                  70                  75                  80

Ser Asp Ser Gly Arg Arg Met Ser Tyr Cys Thr Trp Arg Thr Thr Thr
                85                  90                  95

Gly Ala Thr Gly Ala Ser Ser Gly Arg Lys Ala Ala Ser Cys His
            100                 105                 110

Asn Ser Tyr Val Cys Asn Ser Met Thr Ser Ser Lys
        115                 120

<210> SEQ ID NO 11
<211> LENGTH: 123
<212> TYPE: PRT
<213> ORGANISM: human

<400> SEQUENCE: 11

Ala His Ser His Arg Asp Val His Val Ala Asn Ser Ser Gly Gly Met
1               5                   10                  15

Arg Gly Arg Gly Ala Asp Cys Ala Arg Ala Val Gly Ala Gly Thr Arg
            20                  25                  30

Ala Ser Ser Arg Asp Tyr Ser Val Arg Arg Ala Asp Arg Ala Ala Val
        35                  40                  45

Val Asn Lys Asp Ser Trp Ala Ser Gly Ser Gly Lys Gly Ala Arg Ser
    50                  55                  60

Asp Gly Lys Asp Val Arg His Thr Trp Lys Ser Val Trp His Gly Ser
65                  70                  75                  80

Asp Asn Gly Arg Arg Thr Ser Tyr Cys Thr Trp Arg Thr Ala Ser Ala
                85                  90                  95

Thr Gly Ala Ser Ser Gly Gly Arg Gly Ser Ala Ala Ser Cys His His
            100                 105                 110

Ala Tyr Val Cys Asn Ser Met Thr Ala Ser Lys
        115                 120

<210> SEQ ID NO 12
<211> LENGTH: 15
<212> TYPE: PRT
<213> ORGANISM: Mus musculus
<220> FEATURE:
<223> OTHER INFORMATION: Portion of C terminal fragment of mouse
      Collagen XVIII comprising amino terminus of mouse endostatin

<400> SEQUENCE: 12

His Thr His Gln Asp Phe Gln Pro Val Leu His Leu Val Ala Leu
1               5                   10                  15

```
<210> SEQ ID NO 13
<211> LENGTH: 15
<212> TYPE: PRT
<213> ORGANISM: Homo sapiens
<220> FEATURE:
<223> OTHER INFORMATION: Portion of C terminal fragment of human
      Collagen XVIII comprising amino terminus of human endostatin

<400> SEQUENCE: 13

His Ser His Arg Asp Phe Gln Pro Val Leu His Leu Val Ala Leu
1               5                   10                  15
```